United States Patent
Park et al.

(10) Patent No.: US 10,752,880 B2
(45) Date of Patent: Aug. 25, 2020

(54) THREE-DIMENSIONAL CELL CULTURE SYSTEM AND CELL CULTURE METHOD USING SAME

(71) Applicant: CEFO CO., LTD, Seoul (KR)

(72) Inventors: Hyun Sook Park, Seoul (KR); Sun Ray Lee, Seoul (KR); Ji Won Yang, Seoul (KR); Seol Chu, Suwon-si (KR); Jang Mi Park, Seoul (KR); Hyun Jung Mo, Anyang-si (KR)

(73) Assignee: CEFO CO., LTD, Seoul (KR)

( * ) Notice: Subject to any disclaimer, the term of this patent is extended or adjusted under 35 U.S.C. 154(b) by 45 days.

(21) Appl. No.: 15/512,466

(22) PCT Filed: Sep. 15, 2015

(86) PCT No.: PCT/KR2015/009659
§ 371 (c)(1),
(2) Date: Mar. 17, 2017

(87) PCT Pub. No.: WO2016/043489
PCT Pub. Date: Mar. 24, 2016

(65) Prior Publication Data
US 2017/0283767 A1    Oct. 5, 2017

(30) Foreign Application Priority Data
Sep. 19, 2014  (KR) .................. 10-2014-0125315

(51) Int. Cl.
| | |
|---|---|
| *C12N 5/00* | (2006.01) |
| *C12M 1/12* | (2006.01) |
| *C12M 3/00* | (2006.01) |
| *A01N 1/02* | (2006.01) |
| *A61K 35/12* | (2015.01) |
| *A61L 27/38* | (2006.01) |
| *A61L 27/60* | (2006.01) |

(52) U.S. Cl.
CPC ............ *C12N 5/0062* (2013.01); *A01N 1/02* (2013.01); *A61K 35/12* (2013.01); *A61L 27/38* (2013.01); *A61L 27/60* (2013.01); *C12M 3/00* (2013.01); *C12M 25/14* (2013.01); *C12N 5/00* (2013.01)

(58) Field of Classification Search
None
See application file for complete search history.

(56) References Cited

U.S. PATENT DOCUMENTS

2014/0206022 A1    7/2014 Nuti et al.

FOREIGN PATENT DOCUMENTS

| JP | 2008-504045 A | 2/2008 |
| JP | 2008-079598 A | 4/2008 |
| KR | 10-2004-0016984 A | 2/2004 |
| KR | 10-2011-0044226 A | 4/2011 |
| KR | 10-2013-0057741 A | 6/2013 |

OTHER PUBLICATIONS

Li et al., Oncology Reports, vol. 32: pp. 539-547, 2014, Epub date Jun. 13, 2014.*
Corning.com, Permeable Membranes, retrieved from the internet Nov. 29, 2018: https://www.corning.com/worldwide/en/products/life-sciences/products/permeable-supports/transwell-snapwell-netwell-falcon-permeable-supports.html.*
Guzman et al., Abstract, International Journal of Pharmaceutics, vol. 80, Issues 1-3, 1992, pp. 119-127.*
Patel et al., Trends Biomater. Artif. Organs, 25(1), 20-29 (2011).*
Vashi et al., Biomaterials 29 (2008), pp. 573-579.*
Ma Zhiwei et al., Chitosan Hydrogel as siRNA vector for prolonged gene silencing, Journal of Nanobiotechnology, Jun. 19, 2014, vol. 12 Article No. 23, Internal pp. 1-9.
Huaping Tan et al., Injectable, Biodegradable Hydrogels for Tissue Engineering Applications, materials, Mar. 10, 2010, 1746-1767.

* cited by examiner

*Primary Examiner* — Scott Long
*Assistant Examiner* — Evelyn Y Pyla
(74) *Attorney, Agent, or Firm* — Novick, Kim & Lee, PLLC; Jae Youn Kim

(57) ABSTRACT

A three-dimensional cell culture method on the basis of a biodegradable synthetic hydrogel is provided. The method may include culturing cells in a cell culture dish in a non-contact manner using a porous membrane and a biodegradable synthetic hydrogel in the culture of stem cells and primary cells.

7 Claims, 6 Drawing Sheets

THREE-DIMENSIONAL CELL CULTURE SYSTEM AND CELL CULTURE METHOD USING SAME

TECHNICAL FIELD

The present disclosure relates to a three-dimensional cell culture method on the basis of a biodegradable synthetic bio-gel and, more specifically, to a method for culturing cells in a cell culture dish in a non-contact manner using a porous membrane and a biodegradable synthetic bio-gel in the culture of stem cells and primary cells.

BACKGROUND ART

The most widely used cell culture method is currently to culture cells in a two-dimensional well plate or culture dish. However, according to recent papers, two-dimensional (monolayer) cell culture causes lower cell functions and significantly changed morphology compared with three-dimensional cell culture (Proc. Natl. Acad. Sci. USA, 100: 1943-1948, 2003; Cell, 111: 923-925, 2002; Cancer Cell 2: 205-216, 2002). In order to overcome these disadvantages, cell culture methods using three-dimensional structured supports have been recently developed, and electrospinning, foam molding, method ionic concentration, and making inversion structures using spherical self-assemblies are widely employed as methods for making such structures. In recent years, a new paradigm of cell culture method that creates an environment similar to the in vivo environment has been attempted through the development of the field of a bio-MEMS, called DNA chips, protein chips, and integrated chips, which is a microelectromechanical system used in the biomedical field (Proc. Natl. Acad. Sci. USA, 96: 5545-5548, 1999; Anal. Chem., 74: 1560-1564, 2002; Biotechnol. Prog., 20: 338-345, 2004; Biomed. Microdevices, 4: 161-166, 2002). Similarly, Korean Patent No. 10-0733914 discloses a three-dimensional microcellular culture system characterized in that cells exist in a three-dimensional gel, but the system has disadvantages in that it is difficult to separate the cells existing in the gel in the cell subculture or analysis using cells after cell culture, and especially, stem cells or primary cells, which are difficult to adhere and proliferate, are damaged during cell separation.

Stem cells refer to cells that can proliferate indefinitely in an undifferentiated state as well as differentiating to have a specialized function and shape under specific environments and conditions. Human embryonic stem cells enable continuous self-renewal under appropriate in vitro culture conditions and have pluripotency to differentiate into all of the cell types that make up the body. Therefore, the application range of study results on human embryonic stem cells is expanding to a wide variety of aspects, such as: the understanding of basic knowledge of development, differentiation, and growth of the human body; the development of cell therapy products for the fundamental treatment of damages or various diseases of the human body; the screening of the efficacy for various novel drug candidates; and the establishment of causes of diseases, the development of therapeutic strategies.

Meanwhile, primary cells refer to cells that are directly primarily cultured from animal tissues or organs, and the primary cells are normal cells obtained from living cells. The primary cells, unlike tumor cells, have a limit in the artificial in vitro subculture. The primary cells are used in the production of biological drugs or the like and have also been developed as cell therapeutics due to an advantage of being similar to an actual biological reaction.

DETAILED DESCRIPTION OF THE INVENTION

Technical Problem

In the conventional cell culture method in which cells are cultured while adhering to a surface of a cell culture container, the permeation of air and the supply of medium nutrients are attained through only a portion of the cells excluding adhering portions thereof, and thus the cell functions deteriorate and the cell morphology varies, resulting in unfavorable growth and proliferation. As for the cells that are hard to adhere, grow, and proliferate, such as stem cells or primary cells, the above-mentioned culture method has a limit, and the conventional three-dimensional culture method allowing the culture inside gels has a disadvantage in that cells cannot be separated, and therefore, there is a demand for the development of a three-dimensional cell culture system facilitating subculture or analysis requiring the separation of cells.

TECHNICAL SOLUTION

Therefore, in order to improve adhesion, growth, and proliferation of stem cells and primary cells by providing air and medium in all directions while allowing easy separation of the cells, an aspect of the present disclosure is to provide a cell culture method for culturing cells in a culture container in a non-contact manner and a cell culture system capable of culturing cells in a non-contact manner in a cell culture container.

Advantageous Effects

In cases where cells are cultured using the cell culture method and the cell culture system of the present disclosure, the cells can be in contact with air and medium in all directions, so that the functions and morphology of the cells are maintained and the adhesion, growth, and proliferation of the cells are promoted; and hydrogels are in a gel phase at a cell culture temperature of 36-37° C., and thus the cells are cultured inside and outside the gel, and the hydrogels are changed into a sol phase at a temperature lower than the cell culture temperature, thereby facilitating the subculture after cell proliferation or the analysis after cell separation, and especially, improving the adhesion, growth, and proliferation of stem cells and primary cells, which are hard to culture.

BEST MODE FOR CARRYING OUT THE INVENTION

Figure 1:
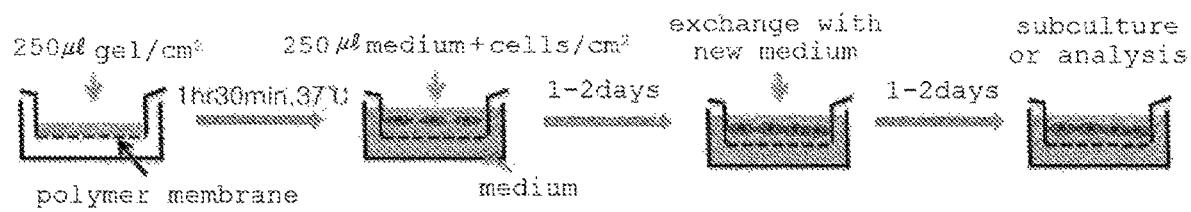
FIG. 1 is a schematic diagram showing a three-dimensional cell culture method and a cell culture system according to the present disclosure.

Hereinafter, the present disclosure will be described in detail with reference to the following examples. However, the present disclosure may be realized in various different forms, and therefore is not limited to embodiments to be described herein.

In accordance with an aspect of the present invention, there is provided a cell culture method, including:

placing a porous membrane inside a cell culture container in a non-contact manner;

applying a biodegradable synthetic bio-gel solution on one surface of the porous membrane to coat a biodegradable synthetic bio-gel through a sol-gel phase transition; and placing a medium containing cells on the coated biodegradable synthetic bio-gel to culture the cells three-dimensionally.

In an embodiment, the porous membrane may be a culture container including a penetrating membrane.

In an embodiment, the porous membrane may be placed in parallel with the bottom of the cell culture container in a non-contact manner. The order of the coating of the biodegradable biosynthetic bio-gel on the porous membrane and the placing of the porous membrane inside the cell culture container in a non-contact manner is not particularly limited. In such a case, the porous membrane may be disposed above the bottom of the cell culture container in a non-contact manner and then the biodegradable synthetic bio-gel may be coated thereon; or the biodegradable synthetic bio-gel may be coated on the porous membrane in advance and then the coated porous membrane may be disposed inside the cell container in a non-contact manner.

In an embodiment, in cases where cells are non-horizontally cultured inside the cell culture container, a biodegradable synthetic bio-gel solution may be applied on one surface of the porous membrane, the cells may be allowed to adhere to the biodegradable synthetic bio-gel, and then the resulting membrane may be placed inside the cell culture container in a non-contact manner.

In an embodiment, the medium flow in between the porous membrane and the cell culture container, such that the medium and air can be provided to even the adhering portion of the cells. The porous membrane and the biodegradable synthetic bio-gel of the present disclosure allow the permeation of air and medium, and the medium flows in to fill a space between the porous membrane and the cell culture container, which is generated by disposing the porous membrane and the cell culture container in a non-contact manner, so that the medium and the air flow into even the adhering portion of the cells, which adheres to the biodegradable synthetic bio-gel, thereby providing nutrients and air necessary for cell culture.

The cell culture container of the present disclosure generally refers to a dish or well plate used for cell culture, and the cell culture container is not particularly limited as long as it is used for cell culture and can introduce a porous membrane to the container bottom in a non-contact manner. In addition, a cell culture container having all-directional air permeability, such as Hyperflask (Corning Co., USA), also corresponds to the cell culture container of the present disclosure.

In an embodiment, the sol-gel phase transition of the biodegradable synthetic bio-gel solution (hydrosol) into the biodegradable synthetic bio-gel may be performed at 37° C. for 1 to 2 hours.

In an embodiment, the biodegradable synthetic bio-gel may include 1-40% biodegradable bio-gels. A biodegradable synthetic bio-gel with a concentration of 40% or more shows an insignificant change in cell growth and proliferation, and thus is meaningless for cell culture. For mesenchymal stem cells, the concentration of the biodegradable synthetic bio-gel is preferably 5-10%, but is not limited thereto.

In an embodiment, the viscosity at 37° C. of the biodegradable synthetic bio-gel may be 1.E+00 to 1.E+06 ($10^0$ to $10^6$) mPa·s depending on the concentration (%) of biodegradable synthetic bio-gel. The biodegradable synthetic bio-gel having a viscosity out of the range does not increase the cell growth and proliferation, causing insignificant cell culture or rather causing the reductions in cell adhesion, growth, and proliferation.

In addition to the biodegradable synthetic bio-gel used in the present disclosure, a porous gel to which cells can adhere may be used. Examples thereof may include HYDROMATRIX™ (Peptide Hydrogel) Peptide Cell Culture Scaffold, prepared by Sigma-Aldrich, D.A. Narmoneva, et al./oligopeptide gel disclosed in Biomaterials 26 (2005) 4837-4846, hydrogel disclosed in WO 2007/029003, hydrogel disclosed in US 20070099840, an oligopeptide matrix for cell adhesion, disclosed in M. Zhou et. al., *Biomaterials,* 2009, in press, a peptide gel disclosed in 4 V. Jayawarna, et al., *Acta Biomaterialia,* 2009, in press, and the like, and any air and medium penetrating gel that adheres to or supports cells is not limited.

In an embodiment, the biodegradable synthetic bio-gel may include at least one of polyester polymers, copolymers of polylactic acid, polyglycolic acid, polycaprolactone, polylactic acid-glycolic acid, copolymers of polyhydroxybutyric acid, poly(hydroxyvaleric acid), and polyhydroxybutyric acid-valeric acid.

In an embodiment, the porous membrane may have a pore size of 0.1-8 µm, but the pore size is not limited as long as the pore size is such that medium and air can pass through the porous membrane but the biodegradable synthetic bio-gel cannot pass through the porous membrane.

In an embodiment, the cells may be stem cells or primary cells. The stem cells may be umbilical cord mesenchymal stem cells (USMSCs), adipose derived mesenchymal stem cells (ADMSCs), or bone marrow-derived mesenchymal stem cells (BMMSCs). The primary cells may be human skin-derived keratinocytes. The stem cells may be derived from mammals, and human-derived and canine-derived stem cells were used in an example of the present disclosure.

As used herein, the term "three-dimensional culture" refers to a culture method in which air and medium are supplied to even a bottom portion of the cell which performs adhesion, so that air and nutrients are supplied to the cells in all directions. In an example of the present disclosure, the biodegradable synthetic bio-gel and the bottom of the cell culture dish were physically separated by the porous membrane, thereby improving adhesion, growth, and proliferation of the cells As used herein, the term "porous membrane", "penetrating membrane", or "polymer membrane" refers to a porous membrane or film type material through which medium or air passes but the biodegradable synthetic bio-gel fails to pass. Any porous structure that is permeable to the cell culture medium and the air is not particularly limited.

As used herein, the term "hydrogel" refers to a material in which a liquid, containing water as a dispersion medium, is solidified through a sol-gel phase transition to lose fluidity and form a porous structure. Any hydrogel suitable for cell adhesion and culture is not particularly limited, and in one embodiment of the present disclosure, a biodegradable synthetic bio-gel was used. The biodegradable synthetic bio-gel of the present disclosure employed a copolymer made of polyoxyethylene-(POE) and polyoxypropylene-(POP-). The biodegradable synthetic bio-gel is in a gel phase, which has a viscosity of 1.E+00 to 1.E+06 ($10^0$ to $10^6$) mPa·s at 36-37° C., and thus facilitates cell adhesion. The biodegradable synthetic bio-gel is changed into a sol phase at a temperature lower than the cell culture temperature, thereby facilitating the subculture after cell proliferation or the analysis after cell separation.

As used herein, the term "stem cells" refers to undifferentiated cells having self-renewal and differentiation potency. Stem cells include sub-groups of pluripotent stem cells, multipotent stem cells, and unipotent stem cells, according to their differentiation capacity. The pluripotent stem cells mean cells that have potency to differentiate into all tissues or cells constituting a living organism, and the multipotent stem cells means cells that do not have potency to differentiate into all kinds but into plural kinds of tissues or cells. Unipotent stem cells mean cells that have potency to differentiate into a particular tissue or cell. The pluripotent stem cells may include embryonic stem cells (ES cells), embryonic germ cells (EG cells), induced pluripotent stem cells (iPS cells), etc. The multipotent stem cells may include adult stem cells, such as mesenchymal stem cells (derived from fat, bone marrow, umbilical cord blood, or umbilical cord, etc.), hematopoietic stem cells (derived from bone marrow or peripheral blood), neural stem cells, germ stem cells, etc. The unipotent stem cells may include committed stem cells for hepatocytes, which are usually quiescent with low self-renewal capacity, but vigorously differentiate into hepatocytes under certain conditions. Examples of the present disclosure verified that the adhesion, growth, and proliferation of cells were promoted by the three-dimensional cell culture method of the present disclosure using bone marrow-derived mesenchymal stem cells, adipose derived mesenchymal stem cells, and umbilical cord mesenchymal stem cells as representative samples.

As used herein, the term "primary cells" refers to cells that are isolated from a tissue of an individual without any genetic manipulation, etc., and represents functions of an organ/tissue of a living organism. Primary cells are isolated from skin or vascular endothelium, bone marrow, fat, cartilage, etc., and are used for studying functions of corresponding tissues and cells or as cell therapeutic agents for restoring lost tissues. In examples of the present disclosure, human skin-derived keratinocytes were used.

The origins of the stem cells or primary cells are not particularly limited as long as the cells can be cultured by the cell culture method and cell incubator of the present disclosure, and examples thereof may be cells derived from human, monkey, pig, horse, cow, sheep, dog, cat, mouse, or rabbit. Preferably, the stem cells or primary cells are human-derived stem cells or primary cells, but are not limited thereto.

In accordance with an aspect of the present invention, there is provided a cell culture system, including:

a cell culture container; and a porous membrane having one surface to which a hydrogel is attached, cells being to adhere to the hydrogel, wherein the hydrogel-attached porous membrane is disposed inside the cell culture container in a non-contact manner.

In an embodiment, the porous membrane and the biodegradable synthetic bio-gel are permeable to medium and air, and also are permeable to the cell culture medium, thereby providing nutrients and air necessary for cell culture.

As used herein, the term "cell culture system" refers to a container, an apparatus, or device for culturing cells.

MODE FOR CARRYING OUT THE INVENTION

The present disclosure will be described more detail through the following examples. However, the following examples are provided merely to illustrate the present disclosure and not to restrict the scope of the present disclosure.

EXAMPLES

Example

Stem Cell Culture Method in Three-Dimensional State

Biodegradable synthetic bio-gel (BASF, Germany) was dissolved in sterilized distilled water at concentrations of 5% to 30% at a concentration gradient of 5% to prepare gels with various % values, and then 250 µl/cm2 of the prepared gels were coated on a 0.4 µm to 1 µm-polymer membrane (Corning, USA), and solidified at 37° C. for 1 hour and 30 minutes, thereby manufacturing cell culture containers. Thereafter, human adipose-derived mesenchymal stem cells, human bone marrow-derived mesenchymal stem cells, human umbilical cord mesenchymal stem cells, human skin-derived keratinocyte, or canine-derived mesenchymal stem cells (Canine ADMSC) were seeded on the biodegradable synthetic bio-gels of the cell culture containers, and then cultured in culture medium optimized for respective types of cells in the CO2 incubator at 37° C. for 3-4 days. The human adipose-derived mesenchymal stem cells were cultured in CEFOgro ADMSC medium (CB-ADMSC-GM, CEFO, Korea); the human bone marrow-derived mesenchymal stem cells were cultured in CEFOgro BMMSC medium (CB-BMMSC-GM, CEFO, Korea); the human umbilical cord mesenchymal stem cells were cultured in CEFOgro UCMSC medium (CB-UCMSC-GM, CEFO, Korea); human skin-derived keratinocyte were cultured in CEFOgro HK medium (CB-HK-GM, CEFO, Korea); and the canine-derived mesenchymal stem cells (Canine ADMSC) were cultured in CEFOgro MSGM medium (CB-MS-GM, CEFO, Korea) (FIG. 1).

Comparative Example 1

Stem Cell Culture Method in Two-Dimensional State

Figure 2:
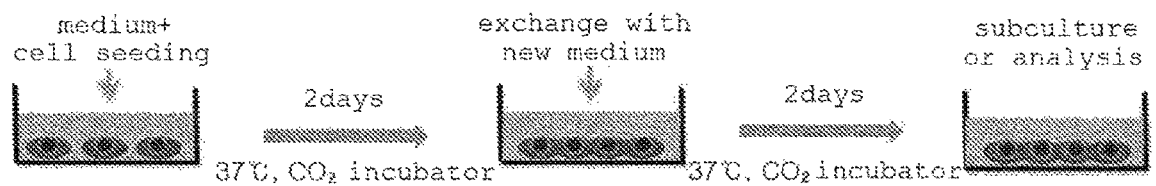
FIG. 2 is a schematic diagram showing a two-dimensional cell culture method using a culture dish according to the conventional art.

Stem cells were cultured by a two-dimensional culture method, which is the conventional stem cell culture method. Specifically, stem cells were seeded in a cell culture container (dish) like in Example above, and then the stem cells were cultured (FIG. 2).

Comparative Example 2

Stem Cell Culture Method in Three-Dimensional State without Polymer Membrane

Figure 3:
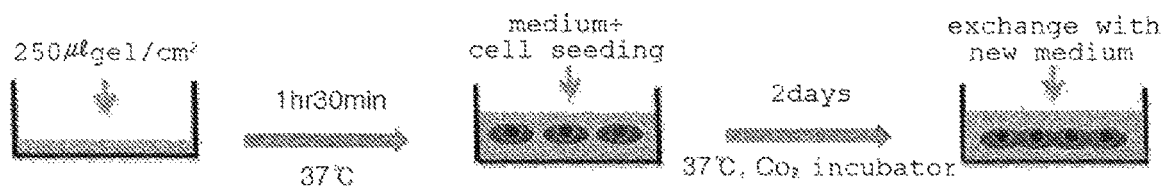
FIG. 3 is a schematic diagram showing a three-dimensional cell culture method and a cell culture system using only a biodegradable synthetic bio-gel.

The biodegradable synthetic bio-gel was coated on the bottom of the cell culture dish without a polymer membrane compared with Example above and then stem cells were seeded thereon in the same manner as in Example above (FIG. 3).

The three-dimensional cell culture method of the present disclosure (FIG. 1) is characterized by providing air and medium to the cells in all directions, compared with FIG. 2 (the two-dimensional method) and FIG. 3 (the three-dimensional method using only biodegradable synthetic bio-gel).

Test Example 1

Figure 4:
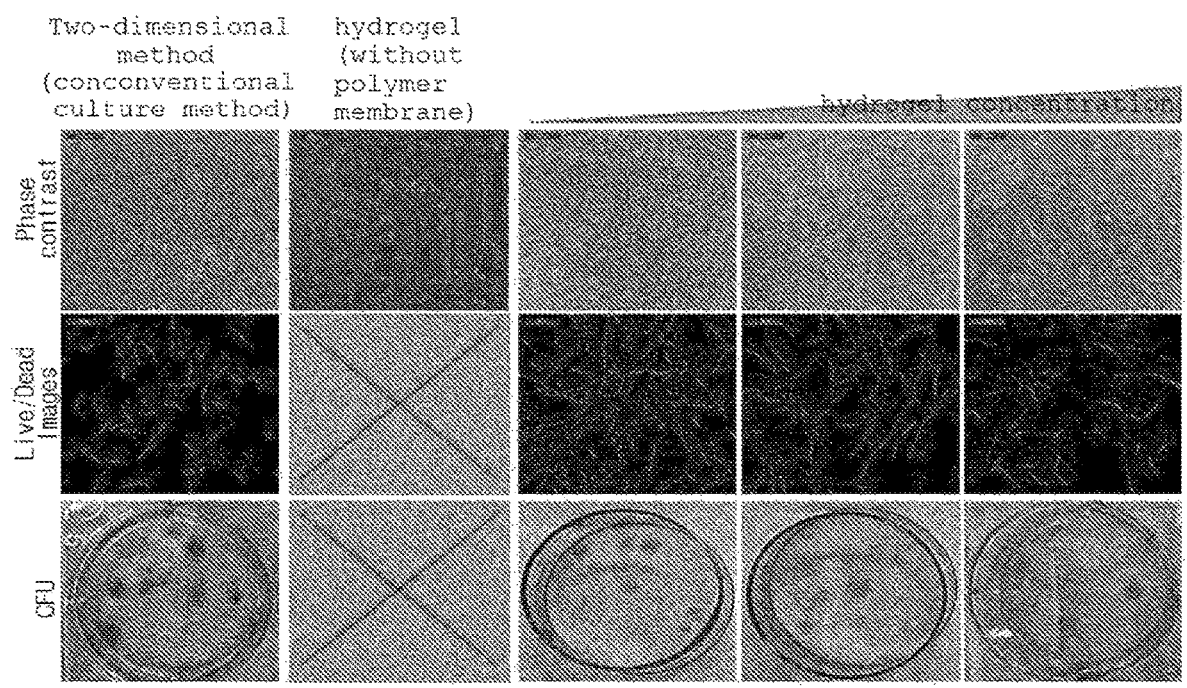
FIG. 4 illustrates cell adhesion condition, cell survival, and colony forming ability of human bone marrow-derived mesenchymal stem cells cultured by a two-dimensional cell culture method using a culture dish according to the conventional art, a three-dimensional cell culture method using only a biodegradable synthetic bio-gel, and a three-dimensional cell culture method according to the present disclosure (5%, 10%, and 15% biodegradable synthetic bio-gels from the third lane to the right).

Verification on Three-Dimensional Culture of Human Bone Marrow-Derived Mesenchymal Stem Cells In order to investigate the cell culture degree after the culture of human bone marrow-derived mesenchymal stem cells, human bone marrow-derived mesenchymal stem cells were cultured by the two-dimensional culture method of Comparative Example 1, the culture method of Comparative Example 3, and the culture method of Example above (5%, 10%, or 15% biodegradable synthetic bio-gels). After the cell culture, the cells were observed under a phase contrast microscope, and as a result, it was verified that the stem cells adhered badly by the method of Comparative Example 2; and the cells were well grown by the method of Example above rather than the two-dimensional culture method (Comparative Example 1) of the conventional art (FIG. 4). Also, in order to confirm the survival of human bone marrow-derived mesenchymal stem cells, the Live/Dead assay in which dead cells are stained red and viable cells are stained green was conducted. For the assay, the cells were cultured as above, and then the medium were removed, and then, without washing, the Live/Dead assay solution (Invitrogen, USA) was added at 150 μl/12 well, followed by reaction at room temperature for 20 minutes. Image analysis was conducted on a fluorescence microscope (LEICA, Germany) immediately after the reaction, without washing, and all these procedures followed the manufacturer's protocol. The results indicated that, like the above observation results by the phase contrast microscope, the cells favorably adhered and grew by the method of Example rather than the method of the comparative example (FIG. 4). In addition, in order to indirectly investigate stem cell potency, CFU analysis was conducted to confirm that one cell divided into cells to form colonies. Specifically, human bone marrow-derived mesenchymal stem cells were seeded at 200 cells per well into a 6-well plate (Corning, USA) by the methods of Example, Comparative Example 1, and Comparative Example 2. After culture for about 8 days, the cells were fixed with formalin and stained with a crystal violet solution (1%). After the staining, the cells were washed with tertiary distilled water or phosphate buffer saline (PBS) and subjected image analysis on an inverted microscope (LEICA, Germany). The results showed similar patterns to the other test results above, and indicated that the stem cells cultured by the method of Example of the present disclosure showed cell division (proliferation) potency in 1-20% biodegradable synthetic bio-gels, especially excellent potency in 5% biodegradable synthetic bio-gels and 10% biodegradable synthetic bio-gels (FIG. 4). Through this, it is considered that when the cells were cultured on the biodegradable synthetic bio-gel directly coated on the culture dish (Comparative Example 2), cell adhesion was unfavorable, and thus, such a culture is not suitable as a cell culture method, and the reason is presumed to be that there is a problem in the permeation of air and the provision of medium.

Test Example 2

Figure 5:
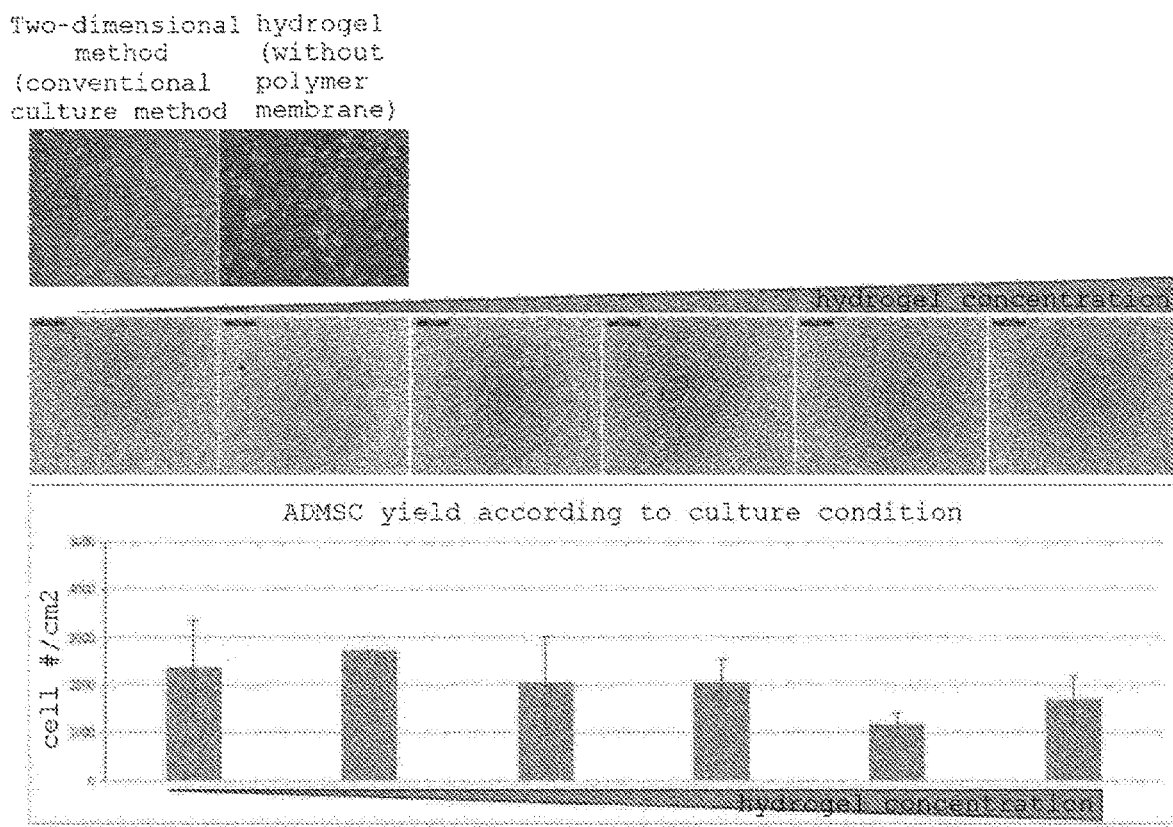
FIG. 5 illustrates cell adhesion condition and cell yield of human adipose-derived mesenchymal stem cells cultured by a two-dimensional cell culture method using a culture dish according to the conventional art, a three-dimensional cell culture method using only a biodegradable synthetic bio-gel, and a three-dimensional cell culture method according to the present disclosure (5%, 10%, 15%, 20%, 25%, and 30% biodegradable synthetic bio-gels toward the right).

Verification on Three-Dimensional Culture of Human Adipose-Derived Mesenchymal Stem Cells In order to investigate the cell culture degree after the culture of human adipose-derived mesenchymal stem cells, human adipose-derived mesenchymal stem cells were cultured by the methods of example (5%, 10%, 15%, 20%, 25%, or 30% biodegradable bio-gel), Comparative Example 1, and Comparative Example 2. After the cells were cultured, the cells were observed by a phase constant microscope. As a result, like the bone marrow-derived mesenchymal stem cells, the cell adhesion was unfavorable in the method of Comparative Example, and most stem cells were well grown when the stem cells were cultured by the method of Example (1 to 30% biodegradable synthetic bio-gels). In addition, in order to count the cultured human adipose-derived mesenchymal stem cells, the cells were cultured by each method, washed twice with PBS, treated with trypsin (Invitrogen, USA), and reacted in a CO2 incubator at 37° C. for 7 minutes. Then, the cells were collected, washed twice with the culture medium, and counted using an automatic cell counter (ADAM; Nano & Tech, Korea). The results were the same as those by the above microscopic observation, and especially, the stem cells cultured by the method of Example showed excellent cell growth in 5-15% biodegradable synthetic bio-gels (FIG. 5).

Test Example 3

Figure 6:
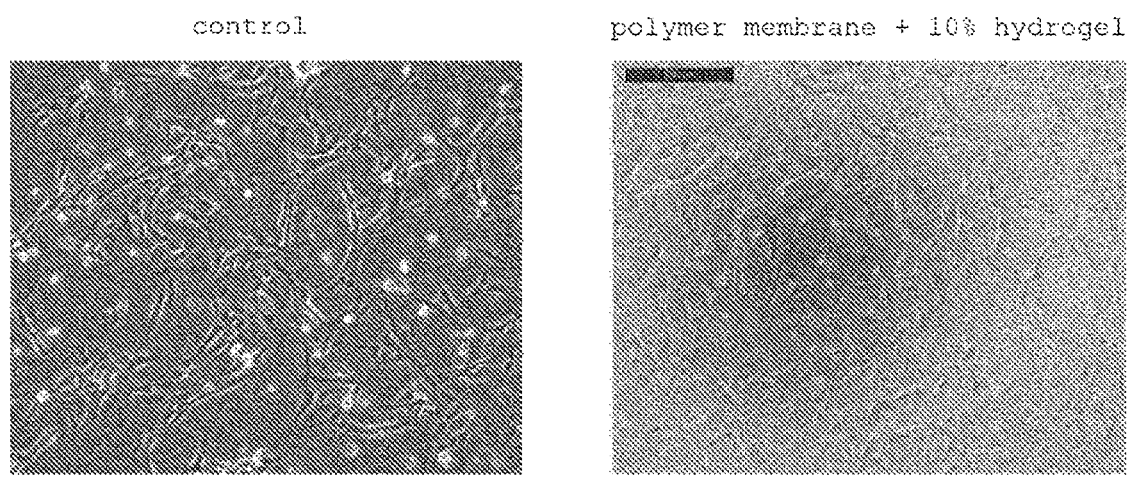
FIG. 6 illustrates human umbilical cord mesenchymal stem cells cultured by a two-dimensional cell culture method using a culture dish according to the conventional art and a three-dimensional cell culture method according to the present disclosure (10% biodegradable synthetic bio-gel).

Verification on Three-Dimensional Culture of Human Umbilical Cord Mesenchymal Stem Cells Human umbilical cord mesenchymal stem cells as another type of stem cells were cultured by the methods of Example (10% biodegradable synthetic bio-gel) and Comparative Example 1, and then observed by a phase contrast microscope. The results indicated that, when the umbilical cord mesenchymal stem cells were cultured by the method using polymer membrane and biodegradable synthetic bio-gel of the present disclosure, the growth of the cells were promoted (FIG. 6).

Test Example 4

Verification on Three-Dimensional Culture of Human-Derived Primary Cells

Figure 7:
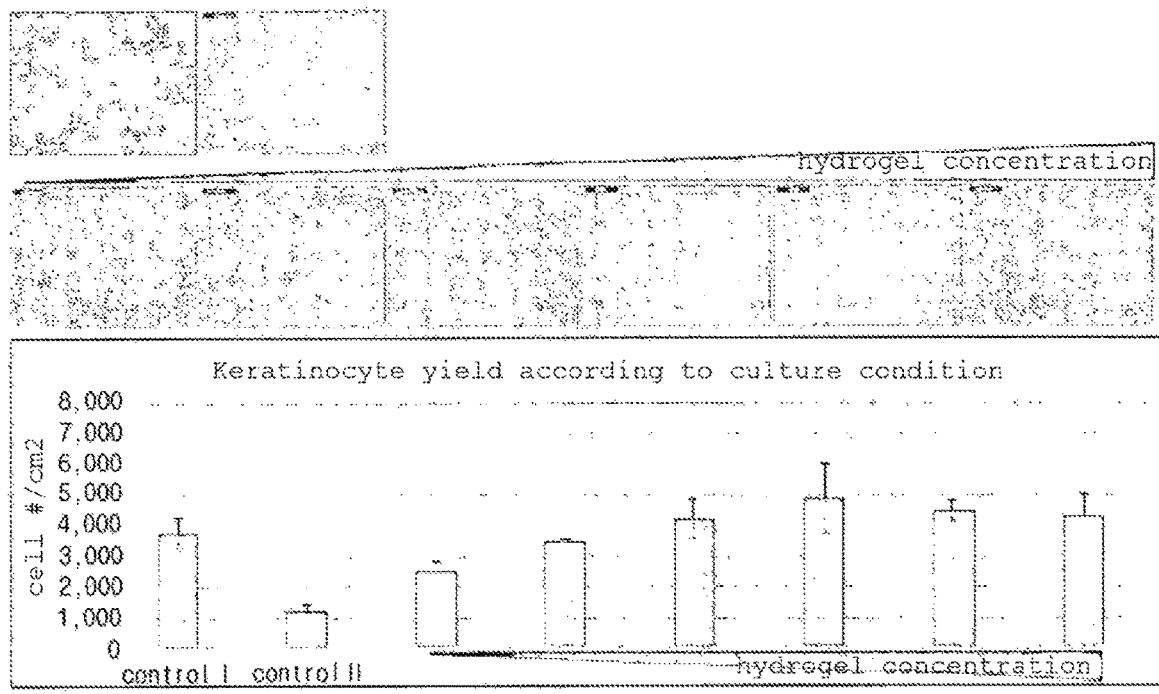
FIG. 7 illustrates cell adhesion condition and cell yield of skin keratinocytes, as human-derived primary cells, cultured by a two-dimensional cell culture method using a culture dish according to the conventional art, a three-dimensional cell culture method using only a porous membrane, and a three-dimensional cell culture method according to the present disclosure (5%, 10%, 15%, 20%, 25%, and 30% biodegradable synthetic bio-gels, toward the right).

Human skin-derived keratinocytes as human-derived primary cells were cultured by the methods of example (5%, 10%, 15%, 20%, 25%, or 30% biodegradable bio-gel), Comparative Example 1, and Comparative Example 2, and then the cell culture degree was investigated. Specifically, human skin-derived keratinocytes were cultured by the methods of example (5%, 10%, 15%, 20%, 25%, or 30% biodegradable bio-gel), Comparative Example 1, and Comparative Example 2, followed by observation by a phase contrast microscope, and then, the cells were collected and counted. As a result, the skin keratinocytes generally grew when the cells were cultured by the method of Example using 1-20% biodegradable synthetic bio-gels solidified on the polymer membranes. As the % of biodegradable synthetic bio-gel was increased, the cell yield was increased. In the 20-30% biodegradable synthetic bio-gels, there was almost no difference according to the content (%) of the biodegradable synthetic bio-gel. Especially, the cell yield was higher in the cell culture container containing 15-30% biodegradable synthetic bio-gels compared with when the cells were cultured in general culture dishes (FIG. 7).

Test Example 5

Figure 8:
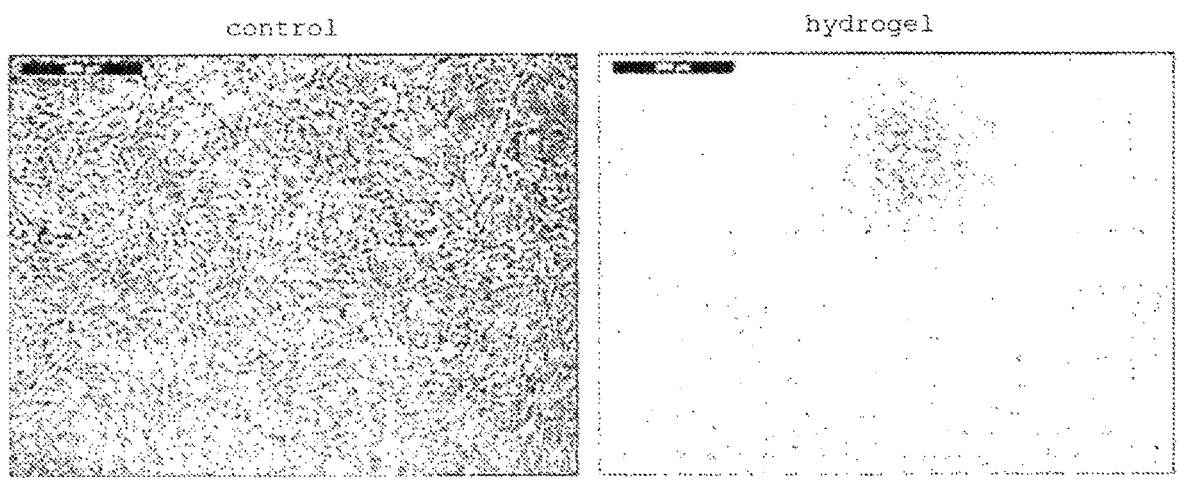
FIG. 8 illustrates canine (beagle) adipose-derived mesenchymal stem cells cultured by a two-dimensional cell culture method using a culture dish according to the conventional art and a three-dimensional cell culture method according to the present disclosure (10% biodegradable synthetic bio-gel).

Verification on Three-Dimensional Culture of Canine-Derived Mesenchymal Stem Cells Canine adipose-derived mesenchymal stem cells as mesenchymal stem cells derived from another species were cultured by the methods of Example (10% biodegradable synthetic bio-gel) and Comparative Example 1, and observed using a microscope. The results indicated that the cells were favorably cultured compared with the two-dimensional culture method (FIG. 8).

It can be seen from the above results that cell adhesion is easy and cell growth and proliferation are promoted when a polymer membrane is formed inside a cell culture dish in a non-contact manner, a biodegradable synthetic bio-gel is formed thereon, and cells are cultured on the biodegradable synthetic bio-gel. Therefore, the use of the cell culture method and the cell culture system of the present disclosure has advantages in that: stem cells and primary cells, which are hard to adhere, grow, and proliferate, can be easily cultured; and the cells can be easily separated for subculture or analysis after culture since the hydrogel is changed into a sol phase.

The invention claimed is:

1. A cell culture method for stem cells or primary cells, comprising:
    placing a porous membrane inside a cell culture container in a non-contact manner;
    applying a biodegradable synthetic hydrogel solution on one surface of the porous membrane to coat the porous membrane through a sol-gel phase transition; and
    placing a medium containing the stem cells or the primary cells on the hydrogel-coated porous membrane to culture the stem cells or the primary cells three-dimensionally,
    wherein the biodegradable synthetic hydrogel is coated at a concentration of 10% when the stem cells are cultured, and a yield of the cultured stem cells is higher than those cultured under a condition that the biodegradable synthetic hydrogel is coated at a different concentration,
    wherein the biodegradable synthetic hydrogel is coated at a concentration of 15 to 30% when the primary cells are cultured, and
    wherein the biodegradable synthetic hydrogel comprises copolymer made of polyoxyethylene-(POE) and polyoxypropylene-(POP-).
2. The method of claim 1, wherein the medium flows in between the porous membrane and the cell culture container to supply the medium with air to cell adhesion sites.
3. The method of claim 2, wherein the porous membrane and the biodegradable synthetic hydrogel allow permeation of the air and the medium.
4. The method of claim 1, wherein the sol-gel phase transition is performed at 37° C. for 1 to 2 hours.
5. The method of claim 1, wherein the biodegradable synthetic hydrogel has a viscosity at 37° C. of 1.E+00 to 1.E+06 ($10^0$ to $10^6$) mPa·s.
6. The method of claim 1, wherein the porous membrane has a pore size of 0.1-8 μm.
7. The method of claim 1, wherein the stem cells are umbilical cord mesenchymal stem cells, adipose-derived mesenchymal stem cells, or bone marrow-derived mesenchymal stem cells.

* * * * *